US005719268A

United States Patent [19]
McEvoy et al.

[11] Patent Number: 5,719,268
[45] Date of Patent: Feb. 17, 1998

[54] ENDOTHELIAL CELL ADHESION MOLECULES

[75] Inventors: Leslie M. McEvoy, Mountain View; Eugene C. Butcher, Portola Valley, both of Calif.

[73] Assignee: The Board of Trustees of the Leland Junior Stanford University, Palo Alto, Calif.

[21] Appl. No.: 338,938

[22] Filed: Nov. 14, 1994

Related U.S. Application Data

[63] Continuation-in-part of Ser. No. 111,827, Aug. 25, 1993, abandoned, which is a continuation of Ser. No. 864,603, Apr. 7, 1992, abandoned.

[51] Int. Cl.$^6$ .......................... C07K 16/18; C07K 16/28; C12N 5/12
[52] U.S. Cl. .................. 530/388.22; 530/388.1; 530/388.2; 435/332; 435/334
[58] Field of Search .................. 435/70.21, 172.2, 435/740.27, 326, 332, 334; 530/388.1, 388.22, 389.5, 388.2

[56] References Cited

PUBLICATIONS

L. McEvoy et al. J. Exp. Med. 185:2069–2077 (1997).
McEvoy Fed and Soc Exp Biol J 6(5) A1888 (1992).
Faruqui et al. Br Heart J 69 (Suppl) 519–529 (1993).
Hakkert et al. Blood 76: 2272–2278 (1990).
Schleff et al. J. Cell Biol 110: 155–163 (1990).
Duijvestison et al. J. Immunol. 138: 713–719 (1987).
Jutila, et al., (1989) Transplantation 48:727–731.
Jutila, et al., (1988) "Homing Receptor in Lymphocyte, Neutrophil and Monocyte Interaction with Endothelial Cells," in Leukocyte Adhesion Molecules: Structure, Function and Regulation, T.A. Springer ed., Springer Verlag, New York; pp. 227–235.
Berliner (1990) J. Clin. Invest. 85:1260.
Bevilacqua (1990) J. Clin. Invest. 76:2003.
Butcher (1990) Am. J. Pathol. 136:3.
Carlos, et al., Blood 77:2266.
Cybulski and Gimbrone (1991) Science 251:788.
Gerrity (1981) Am. J. Pathol. 103:181.
Lewinsohn, et al., (1987) J. Immunology 138:4313.
McEver (1991) J. Cellular Biochem. 45:156.
Territo, et al., (1989) Arteriosclerosis 9:824.

*Primary Examiner*—Paula K. Hutzell
*Assistant Examiner*—Phillip Gambel
*Attorney, Agent, or Firm*—Pamela J. Sherwood; Bozicevic & Reed LLP

[57] ABSTRACT

Methods and compositions are provided for the modulation of monocyte binding to endothelial cells, particularly during inflammatory episodes. Compositions are provided which bind to one or both of the monocyte surface membrane protein or the endothelial surface membrane protein which are complementary or result in the adhesion of the monocyte to the endothelial cell. The subject compositions can be used in diagnosis or therapy.

2 Claims, No Drawings

ENDOTHELIAL CELL ADHESION MOLECULES

CROSS REFERENCE TO RELATED APPLICATIONS

This application is a continuation-in-part of application Ser. No. 08/111,827, filed Aug. 25, 1993 now abandoned, which is a continuation of application Ser. No. 07/864,603, filed Apr. 7, 1992 now abandoned.

This invention was made with Government support under contract GM37734 awarded by the National Institutes of Health. The Government has certain rights in this invention.

INTRODUCTION

1. Technical Field

The field of this invention is the modulation of the monocyte and endothelium response to inflammation, and trafficking of monocytes to sites of inflammation.

2. Background

The migration of leukocytes from the vascular system to the site of injury is an important physiological process for monitoring and treating diseased states. Depending upon the nature of the injury, different types of cells may be recruited. Thus, different groups of leukocytes, such as lymphocytes, neutrophils, or monocytes, or combinations thereof, may be involved. In addition, there appears to be variation in the types or subsets of cells which may be recruited to particular tissues, such as mucosa, lymph node, cutaneous, and the like.

The recruitment of different types of cells, depending upon the nature of the injury, appears to be directed by the presence of surface membrane proteins on both leukocytes, and endothelial cells associated with the vasculature. Some of the surface membrane proteins may be upregulated in response to an agent secreted by the cells at the site of injury. It has generally been found that with each type of cell involved in recruitment and homing, the mobile (usually hematopoietic) cell and stationary (usually endothelial) cells each express a different, interacting surface membrane receptor. These have been referred to in the literature as "receptor and counter-receptor".

There has been substantial progress made in identifying a number of proteins associated with binding of lymphocytes to mucosal tissue and peripheral lymph nodes during extravasation to a site of injury. The process appears to have multiple steps, involving a plurality of proteins on both the lymphocyte and the endothelial cell. While much is understood, there still remains substantial mystery concerning the manner in which the lymphocytes are directed from the vascular system to the site of injury. A similar situation exists with neutrophils. In contrast, the trafficking of monocytes has, for the most part, eluded the identification of proteins which are associated with the transport of the monocytes to sites of injury and disease.

Relevant Literature

Jutila et al., *Transplantation* 48:727–731, 1989; and Jutila et at., "Homing Receptors in Lymphocyte, Neutrophil, and Monocyte Interaction with Endothelial Cells," In *Leukocyte Adhesion Molecules: Structure, Function and Regulation*, T. A. Springer (ed.), Springer-Verlag, New York; pp. 227–235, 1988, describe the binding of various leukocytes to endothelial cells. Berliner (1990) *J. Clin. Invest.* 85:1260 report that low density lipoprotein stimulates monocyte endothelial interactions. The enhancement of adhesion of monocytes to vascular endothelium by interleukin-1 is reported by Bevilacqua et al., ibid. 76:2003. Butcher (1990) *Am. J. Pathok* 136:3 describes mechanisms that direct leukocyte traffic. Carlos et al., *Blood* 77:2266 report the binding of human monocytes to two cytokine-induced adhesive ligands on cultured human endothelial cells: ELAM-2 and VCAM-1. See also Cybulski and Gimbrone (1991) *Science* 251:788. Gerrity (1981) *Am. J. Pathol.* 103:181 describes the role of the monocyte in atherogenesis. Lewinsohn et at. (1987) *J. Immunol.* 138:4313 describes mechanisms for binding of leukocytes with endothelial cells. McEver (1991) *J. Cellular Biochem.* 45:156 describes GMP-140 as a receptor for monocytes on activated platelets and endothelium. Territo et al. (1989) *Arteriosclerosis* 9:824 report that BVLDL pretreatment of endothelial monolayers increases monocyte adhesion.

SUMMARY OF THE INVENTION

Methods and compositions are provided for the regulation of monocyte-endothelial cell binding, particularly during inflammation episodes. Also, screening of compounds affecting the interaction are provided. The subject compounds find use in diagnosis, therapy, and in screening for antagonists.

DESCRIPTION OF THE SPECIFIC EMBODIMENTS

Methods and compositions are provided for modulating and directing the binding of monocytes to endothelial cells at sites of local inflammation. Surface membrane proteins and their counter-receptor proteins, antibodies thereto, and compositions resulting from modifications thereof, are employed in controlling interactions between monocytes and endothelium, directing substances to sites of inflammation associated with monocyte binding, and diagnosing the presence of biological components associated with monocyte-endothelial adhesion. The molecules involved are associated with an adhesion regulatory pathway that differs from the adhesion regulatory pathway for lymphocytes and neutrophils.

The subject compositions are directed to monocyte specific endothelial leukocyte adhesion molecules (M-ELAM) which are up regulated in endothelial cells as a result of stimulation, particularly stimulation as a result of local inflammation, and which result in the increased binding of monocytes. External stimulants in culture which activate the expression of M-ELAM include IL-1, lipopolysaccharide, tumor necrosis factor-α, minimally modified-low density lipoprotein (by minimal modification is intended storage or mild oxidation), and the like.

The subject invention is further directed to receptors which specifically bind to the M-ELAM, in particular the monocyte counter-receptor. By convention, the molecule expressed by the monocyte may be termed a homing receptor (M-homing receptor). Monocytes, as defined herein, are monocytic phagocytes found in the hematopoietic system, and are precursors of tissue macrophages. Monocytes are generally characterized by the cell surface expression of CD14.

Molecules of interest are the receptor and counter-receptor molecules, antibodies which specifically bind to the M-ELAM or M-homing receptor, and nucleic acid sequences encoding the M-ELAM or M-homing receptor. The nucleic acids may be cDNA, a genomic sequence, or a synthetic sequence, or combinations thereof where the composition may be the coding sequenced by itself, in conjunction with transcriptional regulatory regions, associated with a vector, such as a plasmid or virus, or integrated into a genome, particularly a xenogeneic genome.

The pathway, as demonstrated by stimulating in vitro endothelial cells and determining the binding kinetics with monocytes, indicates a relatively slow response when compared to lymphocyte or neutrophil binding, generally requiring greater than about 2 hours to reach maximum binding, frequently from about 2 to 10 hours, where binding of monocytes may then continue for at least an additional 24 hours, more frequently up to about 72 hours.

Monocyte specific binding can be specifically demonstrated in vitro with binding monocytic cells to cultured endothelial cells, e.g. bEnd3 mouse cells (mouse brain-derived polyoma middle T antigen transformed endothelial cell line), human umbilical vein endothelial cells (HUVEC), human aortic endothelial cells (HAEC), etc. stimulated with cytokines, e.g. IL-1, TNFα, etc. An alternative in vitro system utilizes binding of monocytes to frozen sections of high endothelial venules from inflamed lymph nodes. Such inflammation can be induced by injection of complete Freund's adjuvant. Suitable monocytic cells are cell lines such as WEHI 78/24, U937, etc., or normal monocytes, which may be isolated from peripheral blood, bone marrow, lymph, etc., by selection for CD33+ cells, elutriation, density gradient separation, etc. There is substantial complementarity between the human and mouse proteins associated with monocyte binding to endothelial cells, therefore mouse and human cells as the endothelial or monocyte partners are substantially fungible.

Antibodies to the surface membrane proteins are of particular interest. Antibodies to the M-ELAM are obtained by immunizing a xenogeneic immunocompetent mammalian host, including murine, rodentia, lagomorpha, ovine, porcine, bovine, etc. with endothelial cells which have been stimulated with an appropriate stimulant, as described above, usually at least 2 hours prior to immunization, preferably at least about 4 hours prior to stimulation, and usually not more than about 72 hours, more usually not more than about 48 hours. The particular host is primarily one of convenience, and where monoclonal antibodies are desired, having a sufficient supply of splenocytes. Antibodies to the M-homing receptor are obtained by immunizing a host as above with monocytoid cells, e.g. peripheral blood monocytes; cell lines, e.g. WEHI 78/24, U937, etc.

Immunizations are performed in accordance with conventional techniques, where the cells may be injected subcutaneously, intramuscularly, intraperitoneally, intravascularly, etc. Normally, from about $10^6$ to $10^8$ number of cells will be used, which may be divided up into 1 or more injections, usually not more than about 4 injections. The injections may be with or without adjuvant, e.g. complete or incomplete Freund's adjuvant, Specol, alum, etc. If desired, booster injections may be employed at 2 to 4 week intervals, usually there not being more than about 1 to 3 booster injections.

Usually within 3 days after completion of the immunization schedule, the antiserum may be harvested in accordance with conventional ways, to provide polyclonal antisera specific for the surface membrane proteins of the endothelial cells. The antisera will bind to the M-ELAM; or the M-homing receptor, depending on the immunogen. After completion of the immunization schedule the lymphocytes are harvested from the appropriate lymphoid tisue, e.g. spleen or draining lymph node, harvested, and fused with an appropriate fusion partner, usually a myeloma line, producing a hybridoma secreting a monoclonal antibody.

Of particular interest are monoclonal antibodies. The antibodies are characterized by binding to the M-ELAM or M-homing receptor on a cell, where the cell may be any mammalian endothelial or monocytic cell, including both venule and aerial endothelial cells, from any mammalian host, particularly primate, more particularly human. Antibodies of interest will be capable of at least partially blocking the binding of a monocyte to a stimulated endothelial cell. By partially blocking is intended at least 20 percent of the number of cells which bind under the conditions of the screening for binding are inhibited from binding, preferably at least about 25%, and inhibition may be about 50% or more, frequently not more than about 75%. These conditions should be at the least stringent temperature, namely 4° C., preferably at 25° C., more preferably at about 37° C. The M-ELAM specific antibody will be further characterized by not interfering with binding of lymphocytes and neutrophils to stimulated endothelial cells.

Of particular interest are the monoclonal antibodies described in the Experimental section, LM151.7 and 141, and L11, cross-reactive antibodies thereof, i.e. those which substantially completely inhibit simultaneous binding, species analogs thereof, binding fragments thereof, and conjugates thereof. A deposit of the hybridoma cell line (rat× mouse hybrid) LM151 was made at the American Type Tissue Collection, 12301 Parklawn Drive, Rockville Md. 20852, on Apr. 8, 1992, and given the ATCC designation HB 11012. A deposit of the hybridoma cell line (rat×mouse hybrid) L11 was made at the American Type Tissue Collection, 12301 Parklawn Drive, Rockville Md. 20852.

The mouse or other species monoclonal antibodies may be humanized by replacing the constant region, by itself or in combination with one or more conserved framework regions, with regions from human antibodies, so that human IgA, -G, or -M or the like regions may replace the native antibody regions to reduce antigenicity in humans and to provide effector functions.

LM151.7 and 141 are characterized by binding to a protein under Western blot conditions from non-reducing SDS-PAGE gels which has a molecular weight based on standards in the range of about 45–50 kD. The protein is found to be constitutively expressed at low levels by unstimulated endothelium, but is substantially up-regulated within a few hours upon activation of endothelium with IL-1, TNF-α, LPS, or MM-LDL. The antibodies block binding by at least about 25% at both 4° and 25° C. of WEHI78/24 cells to bEnd3 cells.

L11 is characterized by binding at high levels to T lymphocytes, monocytes and neutrophils and with negative to very low binding to B lymphocytes. L11 blocks WEHI78/24 binding to inflamed HEV by greater than 50%, usually by greater than about 70%, and usually not more than about 95%, indicating that the L11 antigen is critically involved in adherence to inflamed endothelial cells. L11 blocks T cell binding to HEV in normal and inflamed peripheral lymph nodes by greater than about 50%, indicating that the L11 antigen is also involved in adherence of T cells to HEV. Similar inhibition is observed in vivo and is associated with increased blood levels of the T cells or monocytes. Furthermore, inhibition of homing is not associated with cell death, as L11 treated lymphocytes return to a normal distribution in recipients over 48 hours.

The subject invention is useful in any species, such as primate, particularly human, domestic animals, e.g. murine, bovine, equine, canine, feline, ovine, porcine, etc., and any of these species may find application as a source of antibodies.

The subject antibodies have a number of in vivo and in vitro uses. The antibodies find use in diagnostics for the detection of inflammation or monocytes. Biological samples, e.g. blood or derivatives thereof, biopsies, synovial fluid, etc. are assayed by any convenient immunoassay for the presence of cells expressing the surface molecule bound by the subject antibodies. Assays may be performed on cell lysates, intact cells, frozen sections, etc. A large number of clinically significant disorders are accompanied by inflammation, e.g. arthritis, bacterial infections, hypersensitivity, wound healing, etc.

The antibodies also find use in screening assays to determine whether a compound is effective in interfering with the interaction between monocytes and stimulated endothelium. In a representative screening assay, the binding of antibodies to frozen sections of inflamed HEV; in vitro stimulated endothelial cells, monotyes, etc. is measured. Compounds, particularly peptides, aptamers, carbohydrates, small organic molecules, etc. are added to the mixture of antibody and cells, and it is determined whether there is a reduction in antibody binding, as indicative that the compound reacts with the adhesion molecule. Alternatively, purified or semipurified M-ELAM or M-homing receptor may be bound to an insoluble substrate, and used in lieu of the cells or tissue.

Another aspect of the invention is the targeting of therapeutic or diagnostic reagents (radiotoxins, reagents capable of inducing vascular permeability to enhance access of soluble blood-borne macromolecular reagents to surrounding tissues or neoplasms, or radiologic, nuclear magnetic resonance or other imaging reagents) to specific tissues or organs. Reagents are covalently linked, using conventional techniques, to the subject antibodies or other specific binding molecule to tissue-specific endothelial cell ligands or molecules, and injected intravenously to localize along the vasculature in the target organ or tissue. Such targeting allows novel imaging approaches to the diagnosis of vascular abnormalities, or to the evaluation of the vascularization of malignancies. For example, rheumatoid arthritis is known to be associated with inflammation, and imaging reagents injected intravenously might readily identify sites of pre-symptomatic inflammation episodes. This approach to imaging, based on changes in the surface of endothelial cells in the local vasculature, avoids the problem of delivery of macromolecules to extravascular sites. The invention also permits localized targeted delivery of therapeutic agents to selected tissues or organs.

The ability to inhibit immune system functions is known to be therapeutically useful in treating a variety of diseases, among them are autoimmune and related disorders, e.g. systemic lupus erythematosus, rheumatoid arthritis, polyarteritis nodosa, polymyositis and dermatomyositis, progressive systemic sclerosis (diffuse scleroderma), glomerulonephritis, myasthenia gravis, Sjogren's syndrome, Hashimoto's disease and Graves' disease, adrenalitis, hypoparathyroidism, and associated diseases; pernicious anemia; diabetes; multiple sclerosis and related demyelinating diseases; uveitis pemphigus and pemphigoid; cirrhosis and other diseases of the liver; ulcerative coliris; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.

The antibodies or other epitope-binding molecules used in the method of the present invention are preferably administered to individuals, preferably mammals, in a manner that will maximize the likelihood of the antibody or other epitope-binding molecule reaching the targeted cell, binding to k, and thereby blocking the interaction of circulating monocytes and endothelial cells. This in turn will inhibit or divert monocyte traffic through particular sites and thus control certain neoplastic or dysfunctional diseases. Carbohydrates can also find use to act as inhibitors, as well as other molecules which specifically bind to the M-ELAM or M-homing receptor.

The dose for individuals of different species and for different diseases is determined by measuring the effect of the antibodies or other epitope-binding molecules on the lessening of these parameters which are indicative of the disease being treated. The antibodies or other epitope-binding molecules will normally be administered parenterally, preferably intravenously. Doses of antibodies in a mouse model will generally range from about 0.5–2 mg/host/week for from about 1 to 4 weeks. The dose of the antibody or other epitope-binding molecule may have to be repeated periodically depending upon the particular disease.

When administered parenterally, the antibodies or other epitope-binding molecules will be formulated in an injectable dosage form (solution, suspension, emulsion) in association with a pharmaceutically acceptable parenteral vehicle. Such vehicles are inherently non-toxic and non-therapeutic. Examples of such vehicles are water, saline, Ringer's solution, dextrose solution, and Hanks' solution. Non-aqueous vehicles such as fixed oils and ethyl oleate may also be used. The vehicle may contain minor amounts of additives, such as substances that enhance isotonicity and chemical stability, e.g. buffers and preservatives. The antibody or other epitope-binding molecule is preferably formulated in purified form substantially free of aggregates and other proteins at concentrations of about 1–50 mg/ml. Suitable pharmaceutical vehicles and their formulations are described in Remington's Pharmaceutical Sciences, by E. W. Maxtin, which is incorporated herein by reference.

The endothelial and monocytic cell antigens associated with specific monocyte binding may be obtained in substantially pure form from either natural sources or by recombinant techniques. From natural sources, endothelial cells are stimulated by any of the agents indicated above, or other stimulating agents, and the cells lysed and passed through an affinity column of receptor or monoclonal antibody for the antigen. Monocytes are isolated from natural sources by conventional separation techniques, or cell lines known in the art, may be used as a source of M-homing receptor. The protein is eluted from the affinity column with an appropriate salt solution or aqueous/organic gradient, e.g., acetonitrile, ethanol, etc., usually in the presence of a low acid concentration, 0.1–1 percent trifluoroacetic acid. The eluted protein is then further purified by chromatography, electrophoresis, or the like in accordance with conventional ways. Alternatively, the endothelial cell M-ELAM or M-homing receptor can be obtained by recombinant techniques. Total RNA is isolated from cells which have been shown by antibody binding or by homing behavior to express the targeted protein. Residual DNA may be removed in accordance with conventional techniques and the polyadenylated RNA purified further, on oligo-dT sepharose, gel chromatography, etc. cDNA may then be prepared in accordance with conventional techniques using reverse transcriptase (see Sambrook, et at., supra). The cDNA is then introduced into an appropriate cloning system, such as λgt11, where the cDNA is expressed. The phage plaques are then screened using the subject antibodies, or by employing polyclonal antisera. The cDNA inserts are then subcloned into other vectors, as desired. The cDNA may be used for further probing of the cDNA library for a complete transcript. Alternatively, the cDNA sequence may be used to probe a genomic library to identify the genomic gene encoding the subject proteins (See, for example, Molecular Cloning: A Laboratory Manual, 2nd ed., J. Sambrook, E. F. Fritsch, T. Maniatis, CSHL, Cold Spring Harbor, N.Y., 1989). The subject DNA shall be intended to include the nucleotide sequences encoding the specific proteins, as well as adjacent 5' and 3' non-coding nucleotide sequences involved in the regulation of expression of the protein encoded by the genes, and will include up to about the length of the mature mRNA. Also included in the corresponding genomic sequence, including introns, and may include up to 1 kb of flanking genomic DNA at either the 5' or 3' end, and as much as 10 kb of flanking genomic sequence. These non-coding sequences include terminator and polyadenylation sequences, regulatory protein binding sequences, transcriptional sequences, and the like.

The nucleic acid compositions of the subject invention may be genomic or cDNA sequences encoding all or a part of the subject adhesion and homing molecules. Fragments may be obtained of the cDNA or genomic sequence by chemically synthesizing oligonucleotides in accordance with conventional methods, by restriction enzyme digestion, by PCR amplification, etc. For the most part, fragments will be of at least 12 nt, more usually at least 18 nt. Preferably fragments will include a functional epitope. The sequence providing for a functional epitope can be determined by expression of the sequence, and assaying for reactivity of the expression product with specific antibodies by conventional immunoassay.

The DNA sequences may be obtained in substantial purity, and will be obtained as a sequence other than a sequence of an intact chromosome. Usually, the DNA will be obtained substantially free of other nucleic acid compounds, generally being at least about 50%, usually at least about 90% pure and are typically "recombinant", i.e. flanked by one or more nucleotides with which they are not normally associated with on a natural chromosome.

The DNA sequences may be used in a variety of ways. They may be used as probes for identifying related homing receptors and ELAMs in the same, or other species. Homologous sequences are those with substantial sequence similarity to M-homing receptor and M-ELAM sequences, i.e. at least 80%, preferably at least 90%, more preferably at least 95% sequence identity with the nucleotide sequence. Such homologous nucleic acid sequences will be detected by hybridization under low stringency conditions, for example, at 50° C. and 10XSSC (0.9 M saline/0.09 M sodium citrate) and remain bound when subject to washing at 55° C. with 1XSSC.

The DNA may also be used to identify cells or organs which are expressing the subject genes. The manner in which one probes cells for the presence of particular nucleotide sequences, particularly as DNA, mRNA or cDNA, is well-established in the literature and does not require elaboration here. Conveniently, mRNA may be isolated free of DNA, and by using reverse transcriptase and PCR with primers specific for the various allergens, the subject cDNAs of may be expanded, separated on gel electrophoresis and then probed using Southern blotting or sequencing. Other techniques may also find use.

For expression, the DNA sequences may be inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly *E. coli, B. subtills,* mammalian cells, such as CHO cells, COS cells, monkey kidney cells, lymphoid cells, particularly human cell lines, and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc., are of particular interest.

Expression cassettes may be prepared comprising the transcription initiation region, which may be constitutive or inducible, with or without an enhancer sequence, including the endogenous or heterologous enhancer sequence, the gene encoding the subject allergens or fragment thereof, and a transcriptional termination region, optionally having a signal for attachment of a poly A sequence. The gene may be genomic, including the native introns, or cDNA gene, or portion thereof. Of particular interest is the use of sequences which allow for the expression of functional epitopes, usually at least about 24 nucleotides in length, more usually at least about 48 nucleotides in length, and up to the complete open reading frame of the gene.

After introduction of the DNA, the cells containing the construct may be selected by means of a selectable marker, the cells expanded and then used for expression. Where secretion is desired, a signal peptide may be joined to the sequence encoding the subject proteins or fragments thereof, whereby the protein will be expressed, translocated through the cell membrane, and processed to remove the signal peptide.

The expression cassettes may be introduced into a variety of vectors, where the vectors will normally be characterized by the ability to provide selection of cells comprising the expression vectors. The vectors may provide for extrachromosomal maintenance, particularly as plasmids in bacteria or viruses in eukaryotic cells, or for integration, particularly in mammalian cells. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker which is chosen will be selected in accordance with the nature of the host, where in some cases, complementation may be employed with auxotrophic hosts, e.g. yeast. Introduction of the DNA construct may be by any convenient means, e.g. calcium-precipitated DNA, electropotation, fusion, transfection, infection with viral vectors, etc.

Fragments of the M-ELAM or M-homing receptor may be used to interfere with the binding between monocytes and endothelial cells. Soluble forms of the M-ELAM can serve to bind to the M-homing receptor, and inhibit binding to the M-ELAM, where the soluble form is a protein or fragment thereof, a carbohydrate, glycoprotein, or other molecule capable of mimicking a portion of the M-ELAM which binds to the M-homing receptor. Soluble forms of the M-homing receptor serve to bind to the cell adhesion molecules of the endothelial cell, and inhibit binding to the M-homing receptor, where the soluble form can be a protein or fragment thereof, a carbohydrate, glycoprotein, or other molecule capable of mimicking a portion of the M-ELAM which binds to the M-homing receptor. The M-homing receptor is also involved in the regulation of T cell homing, and can be further used to block the interaction of T cells with endothelial cells.

These proteins may include sequences having the same or substantially the same sequence as the M-ELAM or M-homing receptor, anti-idiotypes, where the anti-idiotype binds to an antibody which binds to the M-ELAM, carbohydrate portions of the M-ELAM which bind to a lectin portion of the monocyte cell adhesion molecule, and the like.

For targeting various molecules to post-capillary venules associated with monocyte binding, specific binding molecules, ligands or antibodies may be employed which bind to the M-ELAM. It is not necessary that the specific binding molecules interfere with the binding of the monocyte cell adhesion molecule to the M-ELAM, all that is required is binding to the M-ELAM. The ligands may include carbohydrates which specifically bind to the M-ELAM. The carbohydrate molecules will mimic the sugar portion of the monocyte cell adhesion molecule which binds to a M-ELAM. The sugar molecule may be totally carbohydrate or may have a peptide of fewer than 50, usually fewer than 30, amino acids.

The peptides of the M-ELAM which are employed for binding to the monocyte cell adhesion molecule will usually be at least about 8 amino acids, more usually at least about 12 amino acids, preferably at least about 16 amino acids, and frequently 20 amino acids or more. Various techniques may be employed to extend the lifetime of the smaller peptides, by using an unnatural amino acid as part of the chain, where the unnatural amino acid does not affect the binding conformation of the peptide, by employing liposomes, by modifying the molecule with stabilizing molecules, such as polyethylene glycol, or the like. The molecules may be administered by any convenient means, particularly parenterally, more particularly intravascularly.

The M-ELAM can be employed for further characterization of the M-homing receptor. Lysates of monocytes, either from appropriate peripheral blood sources of the host or from monocytoid cell lines can be affinity purified, using the M-ELAM, anti-idiotypes which bind to the idiotope of the antibodies to M-ELAM or binding fragments thereof. As described previously, proteins which bind to the affinity column are then eluted and screened for binding to stimulated endothelial cells. By labeling the proteins eluted from the column, one can detect their binding to stimulate endothelial cells, where the endothelial cells may be from native tissue, cell lines, or the like. The proteins and fractions comprising binding proteins are then further purified using the techniques described above. The proteins can also be used for producing antibodies to the proteins for further purification and identification. The protein is sequenced and probes prepared having redundancy, as appropriate, for screening a cDNA library and/or genomic library of monocytes for isolating sequences encoding the monocyte cell adhesion molecule.

The following examples are offered by way of illustration and not by way of limitation.

EXPERIMENTAL

Example 1

Production of monoclonal antibodies binding to M-ELAM.

bEnd3 cells (a mouse brain-derived polyoma middle T antigen transformed endothelial cell line), provided by Werner Risau (Munich) were stimulated with LPS at 1 µg/ml. Four hours after stimulation, $5 \times 10^6$ bEnd3 cells were used to immunize Fisher F344 rats. The cells were suspended in sterile, nonpyrogenic, phosphate buffered saline, and 200 µl of the suspension was injected sub-cutaneously in 4 sites (50 µl per site). The cells were reinjected at 3 week intervals for a total of 4 injections. The rats were sacrificed by cervical dislocation, and their spleens removed. Splenocytes were fused by traditional fusion procedures using the myeloma line SP2/0 as the fusion partner.

Hybridoma supernatants were screened for their ability to inhibit WEHI78/24 (mouse monocytoid cell line) binding to bEnd3 cells. bEnd3 cells were grown on 1 cm×1 cm glass chamber slides. The cells were stimulated for 4 or 18 hours with 1 µg/ml LPS, then washed twice with PBS, and incubated with hybridoma supernatants for 30 minutes at 4° C. WEHI cells ($3 \times 10^5$) were added, and allowed to bind for 30 minutes on a rocking platform at 4° C. Slides were washed once with PBS to remove unbound cells, then placed in PBS with 1% gluteraldehyde to fix the remaining, bound cells. The number of WEHI 78/24 cells bound per field was enumerated by light microscopy.

Several hybridomas were found to secrete monoclonal antibodies that blocked WEHI78/24 binding to 4 and 18 hour LPS-stimulated bEnd3 cells. Three hybridomas (LM151, LM99 and LM141) recognized bands on Western blots of non-reducing SDS-PAGE gels at about 45–49 kD. The hybridomas blocked WEHI78/24 binding to stimulated bEnd3 endothelial cells at 25°, as well as 4° C. The antibodies inhibited WEHI78/24 binding, but not thymocyte binding.

The LM151 antigen was found to be expressed at low levels by unstimulated endothelium and substantially induced on activation of endothelium with IL-1, TNF-a or LPS. The surface expression of the antigen on unactivated vs. activated cells was determined by indirect immunofluorescence and flow cytometric analysis.

Example 2

Monocytoid cell interactions with cytokine-stimulated EC.

Following activation of bEnd3 cells with LPS, IL-1 or TNF-a, as described above, a dramatic increase in binding of WEHI78/24 cells is observed: Increased binding reaches a maximum by 6 h of stimulation and remains unchanged for up to 72 h. This is determined using the assay described in Example 1, but using 2, 4, 6, 8, 12, 24, 48 or 72 hrs. of LPS stimulation. This may be contrasted with kinetics of neutrophil binding, which peak at 4–6 h and return to baseline levels at 12 h.

Blocking studies with monoclonal antibodies specific for known surface adhesion elements were performed with WEHI78/24 cells and LPS-stimulated bEnd3 cells. Anti-integrin subunit a4 antibodies were partially able to block WEHI78/24 binding to LPS-stimulated bEnd3 cells at 4° C. None of the other antibodies against known cell adhesion molecules, LFA-1, MAC-1 and LECAM-1 (L-selectin), as well as control antibody against T200 (the common leukocyte antigen), are able to block and none of the antibodies (including anti-a4) are able to block binding at room temperature. Furthermore, antibodies to ICAM-1 also failed to inhibit binding at 4° and 37° C., while anti-VCAM-1 was able partially to inhibit at 4° C. In contrast, lymphocyte binding under these conditions is substantially inhibited by anti-a4 and anti-VCAM-1 monoclonal antibodies.

Parallel studies with human cells were performed with human umbilical vein endothelial cells (Gimbrone et al. (1976) "Culture of vascular endothelium" in *Progress in Hemostasis and Thrombosis*, Vol. 3, Ed. T.H. Spaet, New York, Grune and Stratton, pp. 1). WEHI78/24 and the human monocyte-like line U937 were examined with LPS-stimulated HUVEC. Neither line was found to bind well to unstimulated HUVEC and binding of both cell types is significantly increased following stimulation with LPS, TNF-a and IL-1.

Anti-α4 MAb was able to block U937 binding at later time points (after about 10 hours) at 4° C., but not at 37° C. Known blocking antibodies against integrin subunit β2 and ICAM-1 failed to block binding of U937 cells to unstimulated, 4 h or 24 h LPS-stimulated HUVECs at 4° or 37° C. Monocyte binding to HUVECs stimulated with LPS for 24–48 h does not appear to involve ELAM-1, since neuraminidase treatment of U937 cells destroys the carbohydrate ligand of ELAM- 1 and diminishes binding of endothelial cells (ECs) treated with LPS for 4 h, but has no effect on U937 binding after 24 or 48 h of LPS stimulation.

To determine the effect of minimally modified-low density lipoprotein (MM-LDL) on monocyte adhesion, second passage HUVECs were either untreated, treated with MM-LDL (10 µg/ml) or with MM-LDL in the presence of cycloheximide (1 µg/ml). Human monocytes purified by elutriation were added for 30 minutes at room temperature. Nonadherent cells were washed away and adherent cells were visually counted. HUVECs treated with MM-LDL exhibit increased human monocyte binding reaching a maximum under 6–10 h, with the increased binding persisting for 72 h and being inhibited by the presence of cycloheximide.

Example 3 cDNA library construction/bacterial expression cloning.

Total RNA is isolated from LPS-stimulated bEnd3 cells (expressing the 151-ELAM antigen by immunofluorescence) by a single step acid guanidinium thiocyanate procedure (Chomczynski et al. (1987) *Anal. Biochem.* 162:156). The RNA is further purified by overnight centrifugation over cesium trifluoroacetate (Pharmacia). Polyadenylated RNA is purified by two rounds of selection using biotinylated oligo-dT and paramagnetic streptavidin particles (Promega). The poly[A⁺]fraction is then used for cDNA synthesis.

The unizap XR cloning system (Stratagene) is employed. The fragments cloned into this vector are rescued with helper phage and recircularized to generate subclones into the Bluescript Sk-phagemid. Single stranded plasmid molecules are obtained by coinfection of *E. coli* carrying the phagemid with M13 helper phage. The single stranded DNA is rescued by retransformation into *E. coli*, aiding in the subsequent generation of cDNA libraries enriched for LPS-inducible transcripts by subtractive hybridization. First strand cDNA is synthesized with an XhoI-dT primer, MuLV reverse transcriptase, and methyl dCTP. After second strand synthesis, ligation of EcoRI adapters and EcoR1 restriction digests, the cDNA is size selected by Sephacryl-S400 spin chromatography. The large cDNAs (greater than 500 bp) are then ligated into the unizap vector, packaged in vitro, and titered. The library comprises $10^7$ independent recombinants with a size range of 700 bp to 2 kb from the bEnd3 cell line.

The unizap cDNA library is plated out on *E. coli* Sure (Stratagene) at about 50,000 plaques/plate and incubated 4 h at 42° C. Duplicate nitrocellulose filters coated with IPTG are applied and the plates are incubated for 4 h per filter at 37° C. Replica filters are washed, blocked with BSA and probed with anti-151-ELAM antisera pre-absorbed to remove reactivity with *E. coli* proteins. Positive clones are identified with an alkaline phosphatase anti-rat IgG, rescreened and plaque purified. (See Goldstein et al. (1989) *Cell*, 56:1063.)

Example 4

Eukaryotic expression cloning.

In this procedure, the COS cell expression/immunoselection system developed by Brian Seed is employed (Seed and Aruffo (1987) *Proc. Natl. Acad. Sci. USA*, 84:3365). The cDM8 vector called pcDNA-1 (Invitrogen) is employed. It is characterized by having (1) a strong promoter element composed of human cytomegalovirus immediate early enhancer sequences fused to Arian sarcoma virus long terminal repeat sequences which provides high level expression in mammalian cells; (2) a small size (4.8 kb) and an origin of replication which allows for high level replication in mammalian cells; and (3) a cloning site which contains compatible restriction sites with the cDNA utilized in the unizap system so as to directly ligate cDNA from the unizap system into the subject vector. The cDNA library is transferred into competent bacteria, followed by transfection into 50% confluent COS cells by polyethylene glycol promoted spheroplast fusion. Seventy-two hours after transfection, the cells are harvested by detaching without trypsin and selected for 151-ELAM expression by panning with monoclonal antibody coated plates and confirming with FACS. Immunoselected cells are lysed, and DNA is transformed back into *E. coli* for additional rounds of transfection/immunoselection.

Example 5

Production of monoclonal antibodies against stimulated human aortic endothelial cells ("HAEC").

Mice are immunized with 24 hour LPS stimulated HAEC as described previously for the immunization of rats with LPS stimulated bEnd3 cells. Hybridoma supernatants are screened initially by immunofluorescence for reactivity with stimulated EC, but no reactivity with unstimulated EC. Unstimulated, and 24 hour LPS stimulated HUECS were stained with hybridoma supernatant, washed to remove unbound antibody, incubated with fluorescently labelled anti-rat antibody, washed to remove unbound antibody, and their fluorescence measured by flow cytometry.

Positive supernatants are tested for their ability to block monocyte adhesion to stimulated EC employing U937 as the human monocytic cell and WEHI78/24 as the mouse monocytic cell. Positive results are confirmed using human peripheral blood monocytes.

The procedure described above is repeated with MM-LDL stimulated HAEC.

Example 6

Isolation of antigens

Salt/detergent extracts of stimulated EC are prepared and screened with ELISA or dot blots for the detection of the antigen. The cells are initially lysed with RIPA (150 mM NaCl, 1.0% NP-40, 0.5% sodium deoxycholate) or CHAPS (3-[cholamidopropyl-10-dimethyl ammonio]-propanesulfonate), 0.1% SDS, 50 mM Tris, pH 8.0). Included in the lysis buffer is a protease inhibitor cocktail consisting of 0.5 mM PMSF, 1 µg/ml aprotinin, 2 mM EDTA, 1 µg/ml pepstatin, and N-ethyl maleimide. The lysate is analyzed by non-reducing and reducing SDS-PAGE and Western blot analysis.

The antigen is immunoprecipitated from extracts of unlabeled, metabolically labeled and iodinated endothelial cells in the manner as described (Berg et al. (1991) *J. Cell Biol.*, 114:343; Streeter et at. (1988) *Nature*, 331:41).

Affinity columns to which are conjugated monoclonal antibodies specific for the antigen are prepared by conjugation of the antibodies to Sepharose 4B. Columns are washed in lysis buffer containing β-octylglucoside (β-OG). Antigens are separated on columns using high pH (100 mM triethylamine, pH 11.5), low pH (100 mM glycine, ph 2–4), and high salt (5 M LiCl and 500 mM NaCl or KCl). Fractions are monitored for protein content and binding to the monoclonal antibodies as well as the cell type having the complementary surface membrane protein.

Example 7

Cell adhesion assays.

Membrane adhesion molecules are eluted from affinity columns in a dialysable detergent (β-OG at 1.5–2X critical micelle concentration (CMC; 50 mM β-OG)). The soluble glycoprotein is concentrated by Amicon filtration and 10–20 µl is added to glass wells of chamber slides (LABTEK, Wilmington, Mass.) containing 40–60 µl of PBS to dilute the detergent below its CMC, wherein the protein binds to the glass. After incubating for 2 h at room temperature, slides are blocked with Dulbecco's modified Eagles medium (DMEM, Applied Scientific, San Francisco, Calif.) containing 10 mM Hepes and 5% newborn calf serum (GIBCO Laboratories, Grand Island, N.Y.). WEHI78/25 cells, human peripheral blood mononuclear cells, human neutrophils, mouse peripheral lymph node (PLN), mesenteric lymph node (LN) and Peyer's patch lymphocytes are applied to the wells. After incubation at 20 min at 4° C., room temperature or 37° C. on a rocking platform, the tops of the slides are removed and slides washed by dipping twice in coplin jars of DMEM and then fixed by incubation in 1.5% glutaraldehyde in DMEM for 1 h.

Human mononuclear and polymorphonuclear cells are isolated from peripheral blood by 1G sedimentation of red blood cells with 0.6% Dextran T500 (Pharmacia, Inc.) followed by centrifugation of the leukocyte-rich supernatant on a discontinuous gradient of 42% and 51% Percoll (Haslett et at. (1985) *American J. Pathol.*, 119:101). Monocytes are separated from the mononuclear cell fraction by a modification of the Recalde method (Fogelman et al. (1988) *J. Lipid Res.*, 29:1243) or by elutriation. Monocyte versus lymphocyte binding wells containing mixed human mononuclear cells are assessed by morphological analysis of Wright stained slides and by flow cytometric analysis of cells removed from the slide by EGTA treatment and stained with lymphocyte specific (anti-Leu4 for T cells and DakopanB for B cells) and monocyte specific (CD14) monoclonal antibodies.

Binding of antigen to monocytes establishes the monocyte-ELAM antigen, while binding HUVEC or HAEC establishes the monocyte cell adhesion molecule.

Example 8

L11 Monoclonal antibody

Materials and Methods

Monoclonal Antibody Generation. WEHI78/24 cells were grown in DMEM (BioWhittaker, CA) containing 5% fetal bovine serum (Gemini Bioproducts, Inc. Calabasas, Calif.), 5% fetal clone (HyClone, UT) and 2 mM L-glutamine (GIBCO, NY; complete DMEM; cDMEM), washed three times with Hank's balanced salt solution (HBSS), resuspended in HBSS to approximately 50% (v/v) and injected subcutaneously into a Fisher 344 rat. Following three boosts with WEHI78/24 cells approximately 3 weeks apart, the rat was sacrificed by $CO_2$ asphyxiation and the spleen was removed aseptically. The spleen cells were fused with SP2/0 myeloma cells by traditional PEG fusion methods and hybridoma cells were selected and grown in hypoxanthine, aminopterin and thymidine supplemented cDMEM. Hybridoma supernatants were screened for their ability to block binding of WEHI78/24 to confluent IL-1-stimulated bEnd3 cells or to high endothelial venules in inflamed peripheral lymph nodes as previously described. Briefly, bEnd3 cells were seeded into 16 well chamber slides (Miles Scientific) and allowed to grow to confluence, stimulated with 10U IL-1 for 16 hours and washed twice with assay buffer (DMEM without sodium bicarbonate containing 20 mM HEPES, pH 6.9). WEHI78/24 cells were washed twice with assay buffer and resuspended to $6 \times 10^6$ cells per ml in assay buffer. Cells were mixed 1:4 with hybridoma supernatant (50 µl cell suspension plus 150 µl hybridoma supernatant), incubated for 20 min and then added to wells from which the medium was just previously aspirated. Following a 30 min incubation on a rocking platform at 4° C. the top portion of the chamber slide was removed and the slide was dipped twice in assay buffer to remove unbound cells and placed in a coplin jar containing 2% gluteraldehyde in assay buffer. Adherent cells were quantitated by microscopy. The Stamper Woodruff frozen section assay was performed as previously described using inflamed peripheral lymph nodes (prepared by injection of complete Freund's adjuvant 3 days prior to removal). The number of WEHI 78/24 cells bound per HEV was compared to the number of lymphocytes (used as an internal standard) was determined.

The L11 producing hybridoma was subcloned 4 times by limiting dilution and screened by immunofluorescence staining of WEHI78/24 cells analyzed by FACS.

Cellular distribution. Peripheral lymph node- and mesenteric lymph node-derived lymphocytes and bone-marrow derived neutrophils were analyzed by two color flow cytometry. Briefly, cells were harvested from lymph nodes or bone marrow, incubated with L11 MAb or a isotype matched negative control MAb, washed, incubated with a phycoerythrin conjugated mouse anti rat IgG antibody (mouse ant-rat polyclonal antibody; Jackson Laboratories: PE conjugate prepared by Chromoprobe, CA) washed, incubated with 0.5% (v/v) normal rat serum (to block available anti-rat binding sites on the murine anti-rat IgG second stage antibody), washed, incubated with directly FITC conjugated Thy 1.2 (a murine T cell marker), washed and their fluorescence analyzed by flow cytometry.

Frozen sections of mouse Peyer's patches were stained with anti-L11 MAb and isotype matched control antibodies followed by FITC- or PE-conjugated anti-rat antibodies (Jackson Laboratories, West Grove, Pa.). Sections were examined by fluorescence microscopy. T cell zones adjacent to B cell follicles are stained positively where as central B follicles are negative.

Stamper-Woodruff frozen section assay.

HEV normally recruit lymphocytes but not monocytes from the blood. Three days after induction of inflammation by footpad injection of complete Freund's adjuvant, however, circulating monocytes interact avidly with the HEV of draining lymph nodes. This can be modeled in ex vivo binding assays of lymphocytes or the monocyte-like cell binding to frozen sections of lymph nodes; whereas neither monocytes nor monocytoid cells (such as WEHI78/24 cells) bind to uninflamed venules, they bind avidly to inflamed HEV. The ability of anti-L11 MAb to block monocyte and T cell binding to normal and inflamed high endothelial venules was assessed using a modification of the Stamper Woodruff assay as described previously using TRITC-R (Molecular Probes, Eugene OR) labeled rat lymphocytes as an internal standard.

Anti-L11 MAb blocks binding of WEHI 78/24 cells to aortic endothelium from fat-fed rabbits. Aortas from normal New Zealand white rabbits or rabbits placed on a 0.5% cholesterol diet for 2 or 10 weeks were harvested and segments just distal to the subclavian artery were removed, opened longitudinally and immobilized on a 3% agarose gel pre-equilibrated with assay buffer in 35 mm petri dishes. WEHI 78/24 cells were labeled with TRITC, preincubated with either L11 or isotype matched control IgG for 20 min, and $3\times10^6$ were added to the dishes in a final volume of 2 ml. Following a 30 min incubation on a rocking platform at room temperature to allow adherence, and the non-adherent cells were removed by three 5 min washes with 2 ml of assay buffer. Aortas were examined by epi-fluorescence microscopy and the number of adherent cells in 25 fields was counted for each aorta.

In vivo lymphocyte homing.

Lymphocytes from Balb/c mesenteric and peripheral lymph nodes and spleens were labeled with 5 µM Cell Tracker Orange (CMTMR, Molecular Probes, Oreg.) for 30 min at 37° C., washed and treated with either anti-L11 MAb (1 µg/$10^6$ cells) or isotype matched negative control MAb for 20 min. Cells were centrifuged, the supernatant removed, and the cells resuspended in 0.5 ml of HBSS and injected iv. One hour later animals were sacrificed, peripheral blood was collected via heart puncture using a heparinized syringe and lymphocyte suspensions were prepared from spleen, peripheral lymph nodes, mesenteric lymph nodes and Peyer's patches. $1\times10^6$ cells from each suspension were counter stained with FITC conjugated Thy 1.2 and analyzed by flow cytometry. The percentage of homed anti-L11 treated T or B cells in each organ (expressed as the number of CMTMR-labeled (homed) cells/resident cells (T+B) was determined. The frequency of homed anti-L11 treated T or B cells in each organ was determined, and was divided by the frequency of homed cells of the same phenotype in recipients of control anti-body treated cells. Mean results are presented (as % of control MAb-treated cells; Table 3).

In vivo lymphocyte behavior analysis.

Using a previously described live mouse Peyer's Patch preparation under epifluorescent video microscopy (Bargatze and Butcher (1993) *J. Exp. Med.* 178:367–372), the interaction of fluorescently labeled lymphocytes with the high endothelial venules can be observed. Lymphocytes from Balb/c mesenteric and peripheral lymph nodes were labeled with either TRITC (Isomer-R, Molecular Probes, OR) at a final concentration of 2 µg/ml for 20 min at 37° C., in DMEM w/o sodium bicarbonate with 1% fetal bovine serum (Irvine Scientific), 20 mM HEPES pH 7.0, or with CM-FDA (Molecular Probes, OR) at a final concentration of 0.66 µg/ml for 30 min at 37° C. in DMEM w/o sodium bicarbonate with 1% fetal bovine serum, 20 mM HEPES pH 7.0. Cells were layered over 2 ml of BCA and centrifuged at 1000×G for 8 min, washed once with DMEM and resuspended to $5\times10^7$ cells/ml in DMEM. Aliquots were preincubated with isotype matched control MAb or with L11 (1 µg/$10^6$ cells) for 10 rain at room temperature and 0.5 ml ($2.5\times10^7$ cells) injected i.v. The interaction of the injected cells with the high endothelial venules was observed and evaluated as previously described.

Results:

Cellular distribution. Immunofluorescent staining and flow cytometric evaluation of murine leukocytes indicate that L11 antigen is highly expressed by T lymphocytes, monocytes and neutrophils and is negative to weakly expressed by B lymphocytes (staining is just above background staining). This distribution pattern has been confirmed by examining frozen sections of mouse Peyer's patches stained with anti-L11 MAb vs. an isotype matched control antibody. T cell zones adjacent to B cell follicles are stained positively whereas central B follicles are negative. This expression pattern has been compared to those of known T cell markers in Table 2.

TABLE 2

Comparison of expression of L11 and other leukocyte antigens by T cells, B cells, monocytes and neutrophils.

| ANTIGEN | T Cells | B Cells | Monocytes | Neutrophils |
|---|---|---|---|---|
| L11 | + | +/− | + | + |
| CD43 | +/−(bimodal) | +/− | + | + |
| α4 | + | + | + | − |
| β1 | + | + | + | − |
| β7 | +* | +* | − | − |
| L-selectin | + | + | + | + |
| TCR | + | − | − | − |
| CD44 | + | + | + | + |
| CD18 | + | + | + | + |
| CD11a | + | + | + | |
| CD11b | +[4] | +[4] | + | + |
| CD11c | +[2] | +[2] | + | + |
| ICAM-1 | + | + | + | ? |
| ICAM-2[6] | + | − | + | − |
| CD58 (LFA3)[3] | + | + | + | |
| CD31 | +* | − | + | + |
| CD51/CD61 | − | +* | + | − |
| CD2 | + | − | − | − |
| CD4 | +* | − | + | − |
| CD8 | +* | − | − | − |
| CD22 | − | +* | − | − |
| CD23 | + | + | + | + |
| CD36[1] | − | − | + | − |
| cell-CAM 105 | − | − | + | + |
| CD56 (NCAN) | +[5] | − | − | − |

*subset
[1]also on small vessel endothelium and platelets
[2]activated
[3]endothelial cells, epithelial cells and fibroblasts
[4]memory
[5]subset of activated cells
[6]also on endothelium CD43, a major sialoglycoprotein in hematopoietic cells, is the only defined molecule with an expression pattern similar to L11. Double immunoflourescent staining of peripheral lymph node lymphocytes, bone marrow neutrophils and splenic lymphocytes to directly compare expression of L11 and CD43 clearly demonstrates non-identity of the epitopes recognized by these MAbs. Thus, the pattern of L11 expression on normal murine leukocytes is distinct from that of known adhesion or other leukocyte receptors and of the well-defined CD antigens.

Anti-L11 MAb inhibits monocytoid WEHI78/24 cell binding to inflamed HEV.

The relative number of WEHI78/24 cells pretreated with anti-L11 and isotype matched control antibody bound per rat lymphocyte per HEV in inflamed lymph nodes was compared. Anti-L11 blocks WEHI78/24 binding to inflamed HEV by ≧70% indicating that the L11 antigen is critically involved in adherence to inflamed endothelial cells.

Anti-L11 MAb inhibits T lymphocyte binding to normal and inflamed HEV.

The relative number of WEHI78/24 cells pretreated with anti-L11 and isotype matched control antibodies bound per rat lymphocyte per HEV was assessed. Anti-L11 blocks T cell binding to HEV in control and inflamed peripheral lymph nodes by approximately 50% indicating that the L11 antigen is critically involved in adherence of T cells to HEV.

Enhanced binding of WEHI78/24 cells to the lumenal endothelium of aortic segments of cholesterol-fed vs. normal control rabbits is inhibited by MAb L11.

Feeding of New Zealand white rabbits on a high cholesterol diet for 2 weeks results in a dramatic increase in the adhesiveness of aortic endothelium for monocytes in vivo and in our hands, for monocytoid cells in ex vivo assays of WEHI binding to the endothelium of aortic wall segments. MAb L11 is highly effective at inhibiting this interaction (55–98% blockade, N=6). Anti α4 and anti-L-selectin antibodies together inhibit slightly, but are additive with L11. Combined treatment with anti-α4 and anti-L-selectin and L11 MAb almost totally blocks this interaction (n=2).

L11 MAb inhibits short term homing of T lymphocytes to lymphoid organs

Pretreatment of mesenteric and peripheral lymph node lymphocytes with anti-L11 results in a significant inhibition of homing of T cells (and to a lesser extent B cells) to peripheral lymph nodes, mesenteric lymph nodes, Peyer's Patches and spleen (Table 4). A substantial increase in the number of circulating T cells in the blood is also observed (Table 3).

TABLE 3

Anti-L11 MAb blocks homing of T cells to lymphoid organs

| Organ | Percent of Control Cell Homing* | |
|---|---|---|
| | Exp 1 | Exp 2 |
| spleen | 0.47 | 0.36 |
| Peyer's Patch | 0.79 | 0.58 |
| MLN | 0.53 | 0.59 |
| PLN | 0.73 | 0.61 |
| Blood | 1.78 | |

*Control cell homing = 1

As presented in Table 2, anti-L11 MAb inhibits T cell homing from the blood into lymph nodes, Peyer's patches, and spleen. Inhibition appears to reflect blockade of one or more steps involved in T cell-endothelial cell interactions, as fluorescence-tagged lymphocytes accumulate in reduced numbers within the HEV lumen in anti-L11 treated animals, and inhibition is associated with increased blood levels (Table 3, Expt 1). Similar inhibition of T cell trafficking is observed when sample lymphocytes are preincubated with L11 MAb and washed, or injected with excess MAb. Furthermore, inhibition of homing is associated with redistribution and not cell death, as anti-L11 treated lymphocytes return to a normal distribution in recipients over 48 hours (Table 4). Lymph node cells were labeled with CellTracker Orange (10 μM), preincubated with saturating levels of anti-L11 or isotype matched control MAb 9B5, and injected into syngeneic recipients ($10^8$ cells/recipient). As shown in Table 4, 1 hr. homing was blocked by anti-L11, but by 48 hrs. the distribution and number of anti-L11 treated cells in lymphoid tissues was similar to that of control cells.

TABLE 4

Recovery of homing 24 hrs following treatment with anti-L11 MAb

| | Percent of Control Cell Homing* | | |
|---|---|---|---|
| Organ | 1 hour | 24 hours | 48 hours |
| Spleen | 0.2 | 0.8 | 1.0 |
| PLN | 0.2 | 0.8 | 1.1 |
| MLN | 0.3 | 0.9 | 1.2 |
| PP | 0.3 | 0.6 | 1.1 |

*Control cell homing = 1

Evidence that L11 is unique

The cellular distribution of L11 antigen on normal murine cells as well as a number of murine cell lines is distinct from previously described lymphoid antigens. Further, the pattern of inhibition of lymphocyte trafficking by anti-L11 is quite different from that displayed by MAbs to previously characterized adhesion and homing receptors involved in lymphocyte traffic. For example, anti-L-selectin preferentially inhibits homing to PLN>>PP, without influencing splenic homing. Anti-a4 and 137 inhibit PP homing but not PLN or splenic homing. Anti-LFA1 displays partial (~50%) blockade of trafficking to PP and PLN, but not the spleen. Furthermore, unlike L11, each of these known homing receptor pathways is utilized more or less equally by B cells and T cells. Thus the studies presented here provide strong additional support for a unique functional role for L11.

In order to identify novel leukocyte adhesion (and/or adhesion-activating) receptor(s) implied by these functional studies, we produced rat MAbs against WEHI78/24 cells, screening for inhibition of binding to 18 hr LPS-stimulated endothelial cells or to inflamed lymph node HEV. Rat IgG MAb L11 defines protein that is involved in both of these adhesion events, and in adhesion to aortic endothelium from cholesterol fed rabbits (see below). Unlike MAbs to other known monocyte adhesion receptors, L11 reproducibly inhibited adhesion to cytokine-stimulated EC at room temperature, although inhibition rarely exceeded 30%. More dramatically, L11 by itself blocked WEHI78/24 binding to inflamed HEV by ≧70%. These data indicate that the L11 antigen is critically involved in adherence to inflamed EC.

It is evident from the above results, that a number of important diseases can be treated or diagnosed by being able to detect the presence of inflamed endothelial cells which bind to monocytes, to be able to direct specific biological active compounds to the site, and to be able to modulate the interaction between the endothelial cells and the monocytes. In this manner, one may be able to alleviate such diseases as atherosclerosis, allergies, autoimmune diseases, certain malignancies, arthritis, inflammatory bowel diseases, transplant rejection and reperfusion injury. By using the subject compositions, by themselves or in conjunction with the modulation of other leukocyte binding events, one may be able to specifically control inflammatory episodes over extended periods of time.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A monoclonal antibody that specifically binds to the monocyte binding endothelial cell adhesion molecule recognized by the antibody produced by the hybridoma cell line LM151 (ATCC HB11012) wherein said adhesion molecule has a molecular weight in the range of about 45–50 kD as determined by non-reducing SDS-PAGE and wherein said adhesion molecule is constitutively expressed by unstimulated endothelium and is up-regulated upon activation of endothelium with IL-1, TNF-$\alpha$, LPS or MM-LDL.

2. A monoclonal antibody according to claim 1, produced by the hybridoma cell line LM151 (ATCCHB11012).

* * * * *